(12) United States Patent
Arie et al.

(10) Patent No.: US 7,704,697 B2
(45) Date of Patent: Apr. 27, 2010

(54) **PROTEIN WHICH CAN BE USED, IN PARTICULAR, FOR THE IN VITRO ISOLATION AND PREVENTION OF *LEGIONELLA PNEUMOPHILA* INFECTIONS**

(75) Inventors: Jean-Philippe Arie, Lyons (FR); Camille Cyncynatus, Antony (FR)

(73) Assignees: InGen BioSciences, Chilly Mazarin (FR); Universite Claude Bernard Lyon 1, Villeurbanne (FR)

( * ) Notice: Subject to any disclaimer, the term of this patent is extended or adjusted under 35 U.S.C. 154(b) by 21 days.

(21) Appl. No.: 11/659,334

(22) PCT Filed: Jun. 21, 2005

(86) PCT No.: PCT/FR2005/001549

§ 371 (c)(1),
(2), (4) Date: May 5, 2008

(87) PCT Pub. No.: WO2006/027431

PCT Pub. Date: Mar. 16, 2006

(65) Prior Publication Data

US 2008/0260767 A1 Oct. 23, 2008

(30) Foreign Application Priority Data

Aug. 6, 2004 (FR) .................................. 04 08714

(51) Int. Cl.
*G01N 33/53* (2006.01)
*C12N 9/00* (2006.01)
*C12N 9/10* (2006.01)
*C07K 14/00* (2006.01)
*C07K 17/00* (2006.01)

(52) U.S. Cl. .................... 435/7.1; 435/183; 435/193; 530/350

(58) Field of Classification Search .................. None
See application file for complete search history.

(56) References Cited

U.S. PATENT DOCUMENTS 6,248,329 B1 * 6/2001 Chandrashekar et al. . 424/191.1

FOREIGN PATENT DOCUMENTS

WO WO 2005/049642 * 6/2005

OTHER PUBLICATIONS

Invitrogen product catalog 1997—Primers for First-strand cDNA synthesis -Under CDNA synthesis and Libraries Chapter.*
Maiwald et al Eur. J. Clin. Microbiol. Infect. Dis., 1995, 14:25-33.*
Bork et al Genome Research 10: 398-400, 2000.*
Definition of Vaccine: The Dictionary of Immunology, Herbert et al eds, Academic Press, 1995.*
Harlow et al , Antibodies A Laboratory Manual, Cold Spring Harbor Laboratory Press Inc., 1988 pp. 23-25, 27-33 and 72-74.*
Greenspan et al, Nature Biotechnology 17:936-937, 1999.*
Colman et al. Research in Immunology 145: 33-36, 1994.*
Houghten et al. New Approaches to Immunization, Vaccines 86, Cold Spring Harbor Laboratory, p. 21-25 and 1986.*
Weeratna et al (Infection and Immunity, Aug. 1994, p. 3454-3462).*
Friedman et al. Seminars in Respiratory Infections Jun. 1998; 13 (2) :100-8.*
Helbig Jurgen H et al: "Clinical utility of urinary antigen detection for diagnosis of community-acquired, travel-associated, and nosocomial legionnaires' disease." Journal of Clinical Microbiology, Feb. 2003, vol. 41, No. 2, Feb. 2003 pp. 838-840, XP002313797 ISSN: 0095-1137 the whole document.
Chien Minchen et al: "the genomic sequence of the accidental pathogen *Legionella pneumophila*." Science. Sep. 24, 2004, vol. 305, No. 5692, pp. 1966-1968, XP0023138520 ISSN: 1095-9203 sequence Q5ZXU7, CR628336.
Cazalet Christel et al: "Evidence in the *Legionella pneumophila* genome for exploitation of host cell functions and high genome plasticity." Nature Genetics. Nov. 2004, vol. 36, No. 11, pp. 1165-1173, XP002313851 ISSN: 1061-4036 sequences Q5X7B7, CR628336.

* cited by examiner

*Primary Examiner*—Robert Mondesi
*Assistant Examiner*—Oluwatosin Ogunbiyi
(74) *Attorney, Agent, or Firm*—Young & Thompson

(57) ABSTRACT

The invention relates to novel polynucleotides, including SEQ ID NO: 1 or parts or variants of the sequence, novel polypeptides encoded by the polynucleotides, expression vectors including the polynucleotides and host cells including the expression vectors. The polynucleotides and polypeptides can be used in the field of in vitro diagnosis and/or for production of vaccines against *Legionella pneumophila*.

2 Claims, No Drawings

PROTEIN WHICH CAN BE USED, IN PARTICULAR, FOR THE IN VITRO ISOLATION AND PREVENTION OF *LEGIONELLA PNEUMOPHILA* INFECTIONS

Novel proteins which can be used, in particular, for the in vitro isolation and the prevention of *Legionella pneumophila* infections.

The present invention relates to the identification of novel polynucleotides and polypeptides, their production and their use in the diagnostic field and/or the production of vaccines against *Legionella pneumophila*.

Legionnaires' diseases are severe respiratory infections resulting from the inhalation of aerosols contaminated with intracellularly growing bacteria of the genus *Legionella*, and which manifest themselves in sporadic or epidemic form. These infections occur both in the city (community infections) and in a hospital environment (nosocomial infections). *Legionella pneumophila* is responsible for 95% of all cases of Legionnaires' disease.

Legionnaires' diseases occur mainly as acute lung infections. They are characterized by the severity of the clinical picture: after an incubation of 2 to 10 days and a pseudo-flu onset, the disease presents a high temperature, general unease, abdominal pain, or even psychological disorders. The radiological impairment is often bilateral. The associated mortality, which is particularly high in some so-called at-risk persons (elderly subjects or subjects suffering from a cancer or a haemopathy), varies from 10 to 20% (13% of the 835 cases recorded in France in 2002).

It is important to be able to make the diagnosis of Legionnaires' disease early because of the therapeutic challenge: indeed, the legionellae are insensitive to the beta-lactams—which are the principal antibiotics prescribed in the event of a pneumopathy—and a specific treatment based on macrolides (erythromycin) or fluoroquinolones has to be used.

Currently, the diagnosis is made by three general methods: the detection of bacteria from bronchopulmonary samples (either directly by immunofluorescence or by culture on selective media); the detection of specific urinary antigens; the detection of a significant increase in the antibody titre in serum (serology).

Direct examination of samples carried out by fluorescence microscopy is performed, for the majority of commercial reagents, with the aid of monoclonal or polyclonal antibodies which recognize all the known serogroups of *L. pneumophila*. The main disadvantage of this technique is its low sensitivity. Its specificity is also imperfect (~90%) because of immunological cross-reactions with certain bacteria such as *Pseudomonas aeruginosa*, *Bordetella pertusis* or *Bacteroides fragilis*. Culture on specific media is the method of choice, in particular with an epidemiological aim (typing of strains), but gives late results since the legionellae grow in 3 to 4 days, or even more.

The urine tests are rapid and very specific. However, their sensitivity is highly variable, 50-90%; this high variability is linked not only to the characteristics of the patient but also to the fact that the current tests only allow the detection of *L. pneumophila* serogroup 1. Finally, in the presence of a positive search for urinary antigens of legionellae, it is essential to carry out in parallel a culture of respiratory samples for the isolation of the bacterium.

Serodiagnosis is most particularly useful in patients who do not produce expectoration and in the event of an epidemiological survey. It is based on the detection of a significant increase in the antibody levels between an early serum and a serum collected 4 to 6 weeks later. About 30% of cases of Legionnaires' disease are currently identified by this method. However, the antigens used in the current tests consist of simple extracts prepared directly from a culture of heat-inactivated legionellae or after inoculation of the bacteria into the vitellin sac of embryonated eggs. The detected antibodies predominantly recognize lipopolysaccharide (LPS) determinants which may be close to LPS determinants of other bacteria and may cause cross-reactions. In fact, reactions of this type have been described with other Gram-negative bacteria such as *Pseudomonas* sp., *Bacteroides* sp., *Bordetella* sp. and some enterobacteria. Finally, most of the current tests only allow the detection of IgG-type antibodies, which requires the taking of two blood samples at an interval of 4-6 weeks in order to make a diagnosis of a recent infection.

In summary, current practices still do not respond to medical expectations for establishing the early diagnosis of Legionnaires' diseases. In particular, current serological tests are based on old detection methods which cannot be automated, or use non-characterized antigens ("antigenic soups") whose specificity and sensitivity are not very satisfactory. The indirect immunofluorescence technique (IFI) is the technique most widely used for serological diagnosis .(McDade J E, Shepard C C, Fraser D W, Tsai T R, Redus M A and Dowdle W R (1977), Legionnaires' disease: isolation of a bacterium and demonstration of its role in other respiratory disease, N Engt J Med. 297 (22): 1197-203). About 70% of the diagnoses in Europe are made by this method. Yet very wide variations exist depending on the patients: thus for an early high titre, the sensitivity is low and the predictive value is very low (of the order of only 10-15%) (Jarraud S, Reyrolle M and Etienne J. in Freney J, Renaud F, Hansen W, Bollet C, Précis de bactériologie clinique, ed. ESKA, Paris, 2000).

No serodiagnostic technique therefore currently uses purified antigens specific for *L. pneumophila*, and allows early diagnosis of the infection.

The protein called 2A1, having the polypeptide sequence SEQ ID No. 2, which is identified from the *Legionella pneumophila* genome, is a protein having no known homologue or function.

The inventors of the present invention have identified novel polynucleotides and novel polypeptides whose possible uses are described below.

Definitions

The following definitions are given in order to facilitate understanding of some of the terms used in this description.

The expression "polynucleotide" is understood to mean a polyribonucleotide or a polydeoxyribonucleotide which may be a DNA or an RNA modified or unmodified.

The term polynucleotide includes, without limitation, a single-stranded or double-stranded DNA, a DNA composed of a mixture of one or more single-stranded regions and of one or more double-stranded regions, a DNA which is a mixture of single-stranded, double-stranded and/or triple-stranded regions, a single-stranded or double-stranded RNA, an RNA composed of a mixture of one or more single-stranded regions and one or more double-stranded regions and the hybrid molecules comprising a DNA and an RNA which may comprise single-stranded, double-stranded and/or triple-stranded regions or a mixture of single-stranded and double-stranded regions. The term polynucleotide may also comprise an RNA and/or a DNA comprising one or more triple-stranded regions. The strands in such regions may come from the same molecule or from different molecules. Consequently, the DNAs or RNAs having modified backbones for stability or other reasons are included in the term polynucleotides. The term polynucleotide is also understood to mean the DNAs and RNAs containing one or more modified bases. The expression modified base is understood to mean, for example, unusual bases such as inosine. The term polynucleotide also relates to the polynucleotides having a chemically, enzymatically or metabolically modified form. The polynucleotides also comprise short polynucleotides such as oligonucleotides.

The expression "polypeptide" is understood to mean a peptide, an oligopeptide, an oligomer or a protein comprising at least two amino acids joined to each other by a normal or modified peptide bond.

The term polypeptide comprises short chains, called peptides, oligopeptides and oligomers, and long chains, called proteins.

A polypeptide may be composed of amino acids other than the 20 amino acids encoded by the human genes. A polypeptide may also be composed of amino acids modified by natural processes, such as the post-translational maturation process or by chemical processes, which are well known to persons skilled in the art. The same type of modification may be present at several sites of the polypeptide and anywhere in the polypeptide: in the peptide backbone, in the amino acid chain or alternatively at the carboxy- or amino-terminal ends.

A polypeptide may be branched following ubiquitination or may be cyclic with or without branching. This type of modifications may be the result of natural or synthetic post-translational processes which are well known to persons skilled in the art.

The expression modifications of a polypeptide is understood to mean, for example, acetylation, acylation, ADP-ribosylation, amidation, covalent binding of flavin, covalent binding of a haem, covalent binding of a nucleotide or of a nucleotide derivative, covalent binding of a lipid or of a lipid derivative, covalent binding of a phosphatidylinositol, covalent or noncovalent cross-linking, ring formation, formation of a disulphide bridge, demethylation, formation of cysteine, formation of pyroglutamate, formylation, gamma-carboxylation, glycosylation, formation of a GPI anchor, hydroxylation, iodization, methylation, myristoylation, oxidation, proteolytic process, phosphorylation, prenylation, racemization, seneloylation, sulphation, the addition of amino acids, such as arginylation or ubiquitination. (PROTEINS STRUCTURE AND MOLECULAR PROPERTIES, 2nd Ed., T. E. Creighton, W.H. Freeman and Company, New York (1993) and Wold, F., Posttranslational Protein Modifications: Perspectives and Prospects, pgs 1-12 in POSTTRANSLATIONAL COVALENT MODIFICATION OF PROTEINS, B. C. Johnson, Ed., Academic Press, New York (1983); Seifter et al., Meth. Enzymol. 182: 626-646 (1990) and Rattan et al., Protein Synthesis: Posttranslational Modifications and Aging, Ann. N.Y. Acad. Sci. 663: 48-62 (1992)).

The expression "isolated" is understood to mean modified by the hand of persons skilled in the art from the natural state, that is to say that the polynucleotide or the polypeptide present in nature has been modified or isolated from its natural environment, or both. For example, a polynucleotide or a polypeptide which is naturally present in a living organism is not "isolated", but the same polynucleotide or polypeptide separated from the materials which coexist in its natural state is "isolated".

The expression "percentage identity" between two polynucleotide or polypeptide sequences is understood to mean the percentage of nucleotides or amino acids that are identical between the two sequences to be compared, which is obtained after the best alignment, this percentage being purely statistical and the differences between the two sequences being randomly distributed over their entire length. Comparisons between two polynucleotide or polypeptide sequences are traditionally carried out by comparing these sequences after having optimally aligned them, the said comparison being carried out per segment or per "comparison window" in order to identify and compare the local regions with sequence similarity. This comparison may be carried out by means of a program, for example the EMBOSS-Needle program (Needleman-Wunsch overall alignment) with the aid of the BLOSUM62 matrix/Open Gap 10.0 and Extension Penalty of 0.5 (Needleman, S. B. and Wunsch, C. D. (1970), J. Mol. Biol. 48, 443-453 and Kruskal, J. B. (1983), An overview of sequence comparison, In D. Sankoff and J. B. Kruskal, (ed), Time warps, strind edits and macromolecules : the theory and practice of sequence comparison, pp. 1-44 Addison Wesley).

The percentage identity is calculated by determining the number of identical positions for which the nucleotide or the amino acid is identical between the two sequences, by dividing this number of identical positions by the total number of positions in the comparison window and by multiplying the result obtained by 100.

A polypeptide having, for example, an identity of at least 95% with the polypeptide SEQ ID No. 2 is a polypeptide comprising, at most, 5 modified amino acids out of 100 amino acids compared with the said sequence. In other words, up to 5% of the amino acids in the sequence SEQ ID No. 2 can be deleted or replaced by another amino acid or the sequence may comprise up to 5% of amino acids in addition compared with the total number of amino acids of the sequence SEQ ID No. 2. These sequence modifications may be located at the amino- and/or carboxy-terminal positions of the amino acid sequence or at any site between these terminal positions, at one or more locations. (Computational Molecular Biology, Lesk, A .M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987).

By analogy, a polynucleotide having an identity of at least 95% with a second polynucleotide is therefore a polynucleotide comprising, at most, 5 modified nucleotides out of 100 nucleotides, compared with the sequence of the said second polynucleotide. In other words, up to 5% of the nucleotides of the said second polynucleotide may be deleted or replaced by another nucleotide, or the said polynucleotide may comprise up to 5% of nucleotides in addition compared with the total number of nucleotides of the second polynucleotide. These modifications may be located at the 3' and/or 5' ends, or at any site between these ends, in one or more locations.

The expression "host cell" is understood to mean a cell which has been transformed or transfected, or is capable of being transformed or being transfected, with an exogenous polynucleotide sequence.

The expression "culture medium" is understood to mean the medium in which the polypeptide of the invention is purified. This medium may consist of the extracellular medium and/or the cellular lysate. Techniques well known to persons skilled in the art also allow them to return the active conformation to the polypeptide if the conformation of the said polypeptide was modified during isolation or purification.

The expression "function" is understood to mean the biological activity of a polypeptide or of a polynucleotide.

The function of a polypeptide in accordance with the invention is that of a *Legionella pneumophila* antigen and that of the polynucleotide in accordance with the invention is to encode this polypeptide.

The expression "antigen" is understood to mean any compound which, alone or in combination with an adjuvant or a carrier, is capable of inducing a specific immune response. This definition also comprises any compound exhibiting structural analogy with the said antigen capable of inducing an immunological response directed against the said antigen.

The expression "structural analogy" is understood to mean analogy both of the primary structure (sequence) and of the secondary structure (structural elements), of the tertiary structure (three-dimensional structure) or of the quaternary structure (association of several polypeptides into a single complex) (BIOCHEMISTRY, 4th Ed, L. Stryer, New York, 1995).

The expression "variant" of a so-called initial polynucleotide or of a so-called initial polypeptide is understood to mean, respectively, a polynucleotide or a polypeptide which differs therefrom by at least one nucleotide or one amino acid, but which keeps the same intrinsic properties, that is to say the same function.

A difference in the polynucleotide sequence of the variant can alter, or not alter, the amino acid sequence of the polypeptide which it encodes, in relation to an initial polypeptide. However, by definition, these variants must confer the same function as the initial polynucleotide sequence, for example, encode a polypeptide having an antigenic function.

The variant polynucleotide or polypeptide generally differs from the initial polynucleotide or the initial polypeptide by one (or more) substitutions, additions, deletions, fusions or truncations or several of these modifications, taken in combination. An unnatural variant of an initial polynucleotide or of an initial polypeptide may be obtained, for example, by site-directed mutagenesis or by direct synthesis.

"Polynucleotide sequence complementary to the polynucleotide sequence" is defined as a polynucleotide which can be hybridized with this polynucleotide sequence under stringent conditions.

The expression "stringent conditions" is generally, but not necessarily, understood to mean the chemical conditions which allow a hybridization when the polynucleotide sequences have at least 80% identity.

These conditions may be obtained according to methods well known to persons skilled in the art.

The expression "antibody" is understood to mean humanized, chimeric, single-chain, monoclonal, polyclonal antibodies, and Fab fragments, including the products of an Fab or of a library for expression of immunoglobulins.

An immunospecific antibody may be obtained by administering a given polypeptide to an animal, followed by recovering of the antibodies produced by the said animal by extraction from its body fluids. A variant of the said polypeptide, or host cells expressing this polypeptide, may also be administered to the animal.

The term "immunospecific" applied to the term antibody, in relation to a given polypeptide, means that the antibody possesses a better affinity for this polypeptide than for other polypeptides known in the prior art.

As indicated above, the subject of the invention is novel polynucleotides, polypeptides, expression vectors comprising the said polynucleotide and host cells comprising the said expression vector, their production, and their use in the production of antibodies, the field of in vitro diagnosis and/or the production of vaccines against *Legionella pneumophila.*

Polynucleotides

The subject of the present invention is in particular an isolated polynucleotide comprising the polynucleotide sequence SEQ ID No. 1 (called 2A1 and extracted from the *Legionella pneumophila* genome). The invention also relates to an isolated polynucleotide comprising:

a) part of the sequence SEQ ID No. 1 having the same function as the sequence SEQ ID No. 1, or b) a polynucleotide sequence having at least 60% identity, preferably at least 80% identity, and better still at least 90% identity, with the polynucleotide sequence SEQ ID No. 1, or with the sequence part as defined under a), and having the same function as the sequence SEQ ID No. 1, or c) a polynucleotide sequence complementary to the polynucleotide sequence SEQ ID No. 1 or to the sequence part defined under a) or to the sequence defined under b).

The present invention also relates to an isolated polynucleotide comprising the sequence SEQ ID No. 1, encoding the polypeptide comprising the amino acid sequence SEQ ID No. 2.

The polynucleotides of the invention may be obtained by standard methods for the synthesis of DNA or RNA.

The polynucleotides in accordance with the invention may also comprise polynucleotide sequences like the noncoding 5' and/or 3' sequences, such as, for example, transcribed sequences, untranslated sequences, splice signal sequences, polyadenylated sequences, ribosome-binding sequences or sequences which stabilize mRNA.

Expression Vectors and Host Cells

The subject of the present invention is also a recombinant vector comprising at least one polynucleotide in accordance with the invention.

Numerous expression systems may be used such as, for example, chromosomes, episomes, derived viruses. More particularly, the recombinant vectors used may be derived from bacterial plasmids, transposons, yeast episome, insertion elements, yeast chromosomal elements, viruses such as baculoviruses, papilloma viruses such as SV40, vaccinia viruses, adenoviruses, fox pox viruses, pseudorabies viruses, retroviruses.

These recombinant vectors may also be derived from cosmids or phagemids. The polynucleotide sequence may be inserted into the recombinant expression vector by methods well known to persons skilled in the art.

The recombinant vector may comprise polynucleotide sequences for controlling the regulation of expression of the polynucleotide and polynucleotide sequences allowing the expression and the transcription of a polynucleotide of the invention and the translation of a polypeptide of the invention, these sequences being chosen according to the host cells used.

The subject of the present invention is also a host cell comprising a recombinant vector in accordance with the invention.

The introduction of the recombinant vector into a host cell may be carried out according to methods well known to persons skilled in the art, such as transfection with calcium phosphate, transfection with cationic lipids, electroporation, transduction or infection.

The host cells may be, for example, bacterial cells such as cells of streptococci, of staphylococci, of *Escherichia coli* or of *Bacillus subtilis*, fungal cells such as yeast cells and cells of *Aspergillus*, cells of *Streptomyces*, insect cells such as cells of *Drosophilia* S2 and of *Spodoptera* Sf9, animal cells, such as CHO, COS, HeLa, C127, BHK or HEK 293 cells or plant cells.

Polypeiptides

The subject of the present invention is also a polypeptide comprising the amino acid sequence SEQ ID No. 2 (called protein 2A1), encoded by the polynucleotide sequence SEQ ID No. 1. The present invention also relates to an isolated polypeptide comprising:

a) part of the amino acid sequence SEQ ID No. 2 having the same function as the sequence SEQ ID No. 2, or b) an amino acid sequence having at least 60% identity, preferably at least 80% identity, and better still at least 90% identity, with the amino acid sequence SEQ ID No. 2, or with the sequence part defined under a), and having the same function as the sequence SEQ ID No. 2.

The subject of the present invention is also a method for preparing a polypeptide as defined above, in which a host cell defined above is cultured and the said polypeptide is isolated from the culture medium.

The polypeptide may be purified from host cells, according to methods well known to persons skilled in the art, such as precipitation with chaotropic agents such as salts, in particular ammonium sulphate, ethanol, acetone or trichloroacetic acid, or means such as acid extraction, ion-exchange chromatography, chromatography on phosphocellulose, hydrophobic interaction chromatography, affinity chromatography, chromatography on hydroxyapatite or exclusion chromatographies.

Antibodies

The subject of the present invention is also a method for producing immunospecific antibodies, and antibodies immunospecific for the polypeptides in accordance with the invention, as defined above.

The immunospecific antibodies may be obtained by administration of a polypeptide according to the invention, of one of its fragments, of an analogue or of an epitope fragment or of a cell expressing this polypeptide, to a mammal, preferably a non-human mammal, according to methods well known to persons skilled in the art.

For the preparation of monoclonal antibodies, it is possible to use customary methods for producing antibodies, from cell lines, such as the hybridoma technique, the trioma technique, the hybridoma technique for human B cells and the EBV hybridoma technique.

Serology

The subject of the present invention is also the use of a polypeptide according to the invention for detecting, in vitro, in biological samples, the presence of antibodies directed against *Legionella pneumophila*.

The invention also relates to the use of antibodies, according to the invention, for detecting, in vitro, in biological samples, the presence of *Legionella pneumophila* antigens.

The invention additionally relates to the use of polypeptides and antibodies according to the invention, for periodically detecting, in vitro, respectively, antibodies directed against *Legionella pneumophila* and *Legionella pneumophila* antigens and thus monitoring the progress of the pathology and of the effect of a treatment applied to a patient.

The biological samples tested may be blood, urine, saliva, serological puncture fluid (for example cerebrospinal fluid, pleural fluid or joint fluid) or one of their constituents (for example serum).

Kits

The subject of the invention is also in vitro diagnostic kits comprising at least one of the polypeptides in accordance with the invention and in vitro diagnostic kits comprising at least one of the antibodies in accordance with the invention.

Vaccines

The present invention also relates to a pharmaceutical composition, which can be used as a vaccine, containing, as active ingredient, at least one polypeptide according to the invention or a polynucleotide or a recombinant vector or a host cell according to the invention.

EXPERIMENTAL PART

A) Protocol for Producing Antigens

Cloning of the Sequence Encoding Protein 2A1

The gene encoding the sequences of the protein 2A1, which is an antigen, is obtained by PCR amplification from the genomic DNA of the bacterium *Legionella pneumophila* (Philadelphia-1 strain, ATCC 33152) using as pair of primers:

the sense oligonucleotide containing the sequence:

```
5'-ACGTTTGTTTTAAAGGAATTTG-3' (SEQ ID NO: 3);
``` and the antisense oligonucleotide containing the sequence:

```
5'-TACGGTCGGTTTGCTGGTC-3' (SEQ ID NO: 4)
```

The corresponding fragment thus amplified is cloned into a vector according to conventional techniques well known to persons skilled in the art. This vector allows the production of the cloned protein under the control of an isopropyl thiogalactoside (IPTG) inducible promoter. The cloned protein corresponds to the amino acid sequence SEQ ID No. 2.

Expression of the Protein 2A1

An *Escherichia coli* strain is transformed with the expression vector described above. The selected bacteria are cultured overnight at 30° C., with shaking, in 30 ml of Luria Bertani medium (LB, J. Miller, "A short Course in Bacterial Genetics", Cold Spring Harbor Laboratory Press, 1992) containing ampicillin at a final concentration of 100 μg/ml. The next day, the culture is diluted 1/50 in a final volume of 1 liter of LB medium supplemented with ampicillin at a final concentration of 100 μg/ml and incubated at 30° C. with shaking. When the turbidity of the culture reaches an absorbance value at 600 nm (A600) of about 0.7, the production of the protein is induced by IPTG at a final concentration of 0.1 mM. The bacteria are harvested by centrifugation (10 minutes at 1400×g and at 4° C.) when the turbidity of the culture reaches an A600 of about 1.5.

Purification

After centrifugation, the cells are resuspended in a 20 mM Tris-HCl buffer at pH 8.0 containing saccharose at 0.5 mM, and then treated with lysozyme (0.2 g/l) in the presence of 12.5 mM ethylenediaminotetraacetic acid (EDTA), DNase, RNase and PMSF (phenylmethylsulphonyl fluoride). The suspension is incubated for 30 minutes at 4° C. and then centrifuged for 10 minutes at 4° C. at 15500×g. The pellet is frozen at −20° C. for at least one night.

After thawing, the bacteria are subcultured in a 25 mM Mes buffer at pH 6.0, and then sonicated 4 times 20 seconds in ice. After centrifugation at 15500×g at 4° C. for 30 minutes, the supernatant is filtered on a membrane with a porosity of 0.22 μm. The filtrate is then deposited on a cation-exchange column (for example SP-Sepharose 12 ml, Amersham Biosciences). After washing the column, the protein is eluted with a linear gradient of 0 to 1 M NaCl in 25 mM Mes [2-(N-morpholino)ethanesulphonic acid] buffer at pH 6.0 in 20 column volumes. The fractions containing the protein are combined and the proteins are precipitated with ammonium sulphate at a final concentration of 0.6 g/l. The solution is left for at least one night at 4° C. and then centrifuged for 30 minutes at 20800×g. The pellet is then taken up in the smallest volume possible (in general 300 μl of 50 mM $Na_2HPO_4$/$NaH_2PO_4$ buffer pH 8.0 containing 100 mM NaCl and then deposited on a gel filtration column, for example SuperdexHR75-10/30, Amersham). The eluted fractions containing the protein are combined and glycerol is added at a final concentration of 20%. The purified proteins are then stored at −20° C. up to their use in the tests.

The concentrations of the proteins are spectrophotometrically determined from the absorption coefficients calculated by the Pace method (Pace C N, Vajdos F., Fee L., Grimsley G. and Gray T., (1995), Protein Science 4, 2411-2423). The purity of the proteins is checked by analysis by SDS-PAGE electrophoresis and by mass spectrometry.

B) Diagnostic Test in Vitro

Sera obtained from patients who have had a documented *Legionella pneumophila* infection (laboratory collection) were used. The infection could be established either by isolation/culture of the bacteria from bronchopulmonary samples, or by demonstrating a seroconversion or by a positive urine test.

The control sera corresponded to sera from blood donors (laboratory collection).

The attachment, to the purified recombinant protein 2A1 (obtained as described above), of the antibodies present in the sera may be evaluated either by Western-blot tests or by the ELISA technique.

Protocol for the Western-blot Test

After transfer, onto a nitrocellulose membrane, of the purified protein 2A1, the membrane is saturated for 30 minutes with the aid of a phosphate buffered saline (PBS) solution containing 3% semi-skimmed milk. After three washings with PBS containing 0.05% polyoxyethylene sorbitan (Tween), the membrane is exposed to the test serum at the appropriate dilution (that is 1/300) in PBS buffer containing 3% semi-skimmed milk for 45 minutes. After three new washings, goat anti-human immunoglobulin G, A, M antibodies (for example 170-6462, Biorad), labelled with alkaline phosphatase, are simultaneously added, for a period of 30 minutes after having been diluted according to the supplier's protocol in PBS buffer containing 3% semi-skimmed milk. Three new washings are carried out and then 5-bromo-4-chloro-3-indolyl phosphate and nitroblue tetrazolium are added according to the supplier's instructions until the result is obtained. A "positive" result corresponds to a precipitation of the substrate on the membrane at the position of 2A1.

Protocol for the ELISA Test

The ELISA plates are left overnight at 4° C. in the presence of 0.5 μg of purified antigen (recombinant protein 2A1) in phosphate buffered saline (PBS). After four. washings with PBS containing 0.05% polyoxyethylene sorbitan (Tween), the plates are saturated for one hour at 37° C. with PBS-Tween containing 5% semi-skimmed milk (250 μl per well). Four new washings are carried out, and then 100 μl of each positive serum, at the appropriate dilution (that is 1/300) in PBS-Tween buffer containing 5% semi-skimmed milk, are added to each well. The plate is then left at 25° C. for 30 minutes. After four new washings, goat anti-human immunoglobulin G, A, M antibodies labelled with alkaline phosphatase are simultaneously added for 30 minutes at 25° C. after having been diluted according to the supplier's protocol in PBS-Tween buffer containing 5% semi-skimmed milk. Four new washings are carried out and then 100 μl of substrate (p-nitrophenyl phosphate), pNPP, for example A-3469, Sigma) are added. The absorbance at 405 nm of each of the wells is measured after an incubation of 30 minutes at 37° C.

Results and Interpretation

A typical result obtained is presented in the table below, knowing that the so-called "positive" sera in this table are those containing antibodies against *Legionella pneumophila* identified by their binding to the polypeptides (antigens) of the invention by Western-blotting:

Table of results for the Western-blot test

| | |
|---|---|
| Number of sera from patients infected with *Legionella pneumophila*, diagnosed according to the prior art and subjected to the diagnosis according to the invention | 24 |
| "Positive" sera among the 24 tested | 18, that is 75% |
| Sera of blood donors as controls | 111 |
| "Positive" sera among the 111 tested | 4, that is 3.6% |

Similar results are obtained by ELISA.

According to the Table, it is observed that, by the Western-blot test or by the ELISA test, at least 70% of the *Legionella pneumophila* infections are identified in vitro by virtue of the antigen according to the invention. The existence, in humans, of a significant antibody response (the probability associated with a $\chi 2$ test is less than 0.05) towards the protein 2A1 during *Legionella pneumiophila* infections, on the one hand, and the fact that the protein 2A1 is relevant for the serological diagnosis of this type of infection, on the other hand, are therefore demonstrated.

Furthermore, the use of the antigen 2A1 according to the invention allows, in some cases, the identification of patients not detected at this stage of the infection (but confirmed in subsequent analyses) by the serological techniques of the prior art.

The invention claimed is:
1. An isolated polypeptide comprising the amino acid sequence of SEQ ID No. 2.
2. A kit for detecting, in vitro, the presence of *Legionella pneumophila* antibodies in biological samples, which kit comprises at least one isolated polypeptide comprising the amino acid sequence of SEQ ID No. 2.

* * * * *

SEQUENCE LISTING

```
<160> NUMBER OF SEQ ID NOS: 4

<210> SEQ ID NO 1
<211> LENGTH: 1332
<212> TYPE: DNA
<213> ORGANISM: Legionella pneumophila
<220> FEATURE:
<221> NAME/KEY: CDS
<222> LOCATION: (1)..(1332)
```

<400> SEQUENCE: 1

| | | | | | | | | | | | | | | | | |
|---|---|---|---|---|---|---|---|---|---|---|---|---|---|---|---|---|
| acg | ttt | gtt | tta | aag | gaa | ttt | gat | gca | cta | aaa | agt | cat | ttt | aac | gac | 48 |
| Thr | Phe | Val | Leu | Lys | Glu | Phe | Asp | Ala | Leu | Lys | Ser | His | Phe | Asn | Asp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acc | gtt | aaa | atc | atc | ctt | caa | cgc | gaa | aaa | aag | gac | aaa | att | gaa | gac | 96 |
| Thr | Val | Lys | Ile | Ile | Leu | Gln | Arg | Glu | Lys | Lys | Asp | Lys | Ile | Glu | Asp | |
| | | | 20 | | | | | 25 | | | | | 30 | | | |

| | | | | | | | | | | | | | | | | |
|---|---|---|---|---|---|---|---|---|---|---|---|---|---|---|---|---|
| ctt | ccc | aac | ccc | aga | aaa | gaa | gag | ctt | caa | ttt | ctg | acc | gct | gtt | ctc | 144 |
| Leu | Pro | Asn | Pro | Arg | Lys | Glu | Glu | Leu | Gln | Phe | Leu | Thr | Ala | Val | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| aat | caa | ttg | gaa | gca | aaa | atc | gat | gaa | ctg | aaa | cca | cgt | tct | ttg | gcc | 192 |
| Asn | Gln | Leu | Glu | Ala | Lys | Ile | Asp | Glu | Leu | Lys | Pro | Arg | Ser | Leu | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| agc | tat | gtc | cat | gta | ttt | tat | ggt | gct | atg | ctg | ctt | gtc | tgt | aaa | gac | 240 |
| Ser | Tyr | Val | His | Val | Phe | Tyr | Gly | Ala | Met | Leu | Leu | Val | Cys | Lys | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtt | gaa | aat | aat | ctg | cgg | gtg | atg | gaa | aag | aaa | gaa | aac | agc | ttg | ctg | 288 |
| Val | Glu | Asn | Asn | Leu | Arg | Val | Met | Glu | Lys | Lys | Glu | Asn | Ser | Leu | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| ttt | act | cgc | tta | atg | gat | ggt | atg | ggt | att | tct | gat | gaa | aat | ata | cca | 336 |
| Phe | Thr | Arg | Leu | Met | Asp | Gly | Met | Gly | Ile | Ser | Asp | Glu | Asn | Ile | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| aca | tct | gag | cag | aac | atc | atg | ttt | tac | aga | gga | tta | aac | aaa | ttc | tta | 384 |
| Thr | Ser | Glu | Gln | Asn | Ile | Met | Phe | Tyr | Arg | Gly | Leu | Asn | Lys | Phe | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| aat | ttc | att | tat | gaa | agc | aat | gat | tct | cgt | aaa | ggc | tta | aaa | aag | gag | 432 |
| Asn | Phe | Ile | Tyr | Glu | Ser | Asn | Asp | Ser | Arg | Lys | Gly | Leu | Lys | Lys | Glu | |
| 130 | | | | | 135 | | | | | 140 | | | | | | |

| | | | | | | | | | | | | | | | | |
|---|---|---|---|---|---|---|---|---|---|---|---|---|---|---|---|---|
| cat | ttc | ctg | caa | gtc | ctt | tcg | tta | aaa | aag | ata | tac | tct | tta | gcc | aaa | 480 |
| His | Phe | Leu | Gln | Val | Leu | Ser | Leu | Lys | Lys | Ile | Tyr | Ser | Leu | Ala | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tta | agt | tat | gag | cag | gaa | gag | gca | gct | gaa | aat | aat | gct | ttg | gca | aaa | 528 |
| Leu | Ser | Tyr | Glu | Gln | Glu | Glu | Ala | Ala | Glu | Asn | Asn | Ala | Leu | Ala | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| tta | act | gct | gat | gga | aaa | acc | aaa | gcc | aat | gcg | aac | agc | ttc | cat | gtg | 576 |
| Leu | Thr | Ala | Asp | Gly | Lys | Thr | Lys | Ala | Asn | Ala | Asn | Ser | Phe | His | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| gaa | aaa | cca | atc | gat | tca | tcc | att | gtt | gag | caa | ttc | aaa | tcc | tgg | gat | 624 |
| Glu | Lys | Pro | Ile | Asp | Ser | Ser | Ile | Val | Glu | Gln | Phe | Lys | Ser | Trp | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| gaa | atg | aaa | ggc | gct | ctt | cat | caa | tta | att | ctc | gat | gaa | ctt | tct | gat | 672 |
| Glu | Met | Lys | Gly | Ala | Leu | His | Gln | Leu | Ile | Leu | Asp | Glu | Leu | Ser | Asp | |
| | | | 210 | | | | | 215 | | | | | 220 | | | |

| | | | | | | | | | | | | | | | | |
|---|---|---|---|---|---|---|---|---|---|---|---|---|---|---|---|---|
| aag | aac | gtt | gct | aaa | att | tca | gct | tta | agt | caa | gcc | cgc | tcc | gca | caa | 720 |
| Lys | Asn | Val | Ala | Lys | Ile | Ser | Ala | Leu | Ser | Gln | Ala | Arg | Ser | Ala | Gln | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctg | aaa | ttt | tta | caa | acg | atg | gca | gaa | caa | cta | gac | aag | atc | cct | aac | 768 |
| Leu | Lys | Phe | Leu | Gln | Thr | Met | Ala | Glu | Gln | Leu | Asp | Lys | Ile | Pro | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| caa | tct | ctt | gag | ccg | tct | gag | aaa | atg | gcc | att | ctt | gct | gga | gca | atg | 816 |
| Gln | Ser | Leu | Glu | Pro | Ser | Glu | Lys | Met | Ala | Ile | Leu | Ala | Gly | Ala | Met | |
| | | | 260 | | | | | 265 | | | | | 270 | | | |

| | | | | | | | | | | | | | | | | |
|---|---|---|---|---|---|---|---|---|---|---|---|---|---|---|---|---|
| tat | atc | gtt | cgt | ggc | caa | ata | gcc | cag | gag | tat | gga | aaa | gat | cca | tta | 864 |
| Tyr | Ile | Val | Arg | Gly | Gln | Ile | Ala | Gln | Glu | Tyr | Gly | Lys | Asp | Pro | Leu | |
| | | 275 | | | | | 280 | | | | | 285 | | | | |

| | | | | | | | | | | | | | | | | |
|---|---|---|---|---|---|---|---|---|---|---|---|---|---|---|---|---|
| agc | aac | gat | aaa | atc | agc | gct | act | gtg | att | cat | aca | ggt | tta | agc | acg | 912 |
| Ser | Asn | Asp | Lys | Ile | Ser | Ala | Thr | Val | Ile | His | Thr | Gly | Leu | Ser | Thr | |
| 290 | | | | | 295 | | | | | 300 | | | | | | |

```
ata ctt cat gcc aat gct gat tgc tgt gaa gac aag gaa gta ctg att      960
Ile Leu His Ala Asn Ala Asp Cys Cys Glu Asp Lys Glu Val Leu Ile
305                 310                 315                 320 gct gct gcg aat aaa ttt att cgt cat atg gtt att gag cgt cct gaa     1008
Ala Ala Ala Asn Lys Phe Ile Arg His Met Val Ile Glu Arg Pro Glu
                325                 330                 335 caa tca aat aaa aaa atc act aag gaa tcc gtt cga gaa aac aac atg     1056
Gln Ser Asn Lys Lys Ile Thr Lys Glu Ser Val Arg Glu Asn Asn Met
            340                 345                 350 ttt tcc gac atc gcc ggc ttc caa ttg atc tct gtc ttg acg tta ata     1104
Phe Ser Asp Ile Ala Gly Phe Gln Leu Ile Ser Val Leu Thr Leu Ile
        355                 360                 365 caa aac atg atc aaa aca tgt cgt act gat gcc att gaa gct tgt gtc     1152
Gln Asn Met Ile Lys Thr Cys Arg Thr Asp Ala Ile Glu Ala Cys Val
370                 375                 380 acc aag cgt aag gaa gaa ctc gaa gca tta aaa ccc aaa aaa gag ggt     1200
Thr Lys Arg Lys Glu Glu Leu Glu Ala Leu Lys Pro Lys Lys Glu Gly
385                 390                 395                 400 tat tcc att gcg agt tca gtc act gga tat gta ggc agc tgg ttt aaa     1248
Tyr Ser Ile Ala Ser Ser Val Thr Gly Tyr Val Gly Ser Trp Phe Lys
                405                 410                 415 aaa gca cca agc atg tct gaa gaa gac gaa gaa gat gac tta aaa gat     1296
Lys Ala Pro Ser Met Ser Glu Glu Asp Glu Glu Asp Asp Leu Lys Asp
            420                 425                 430 caa aac aca gca gaa gag acc agc aaa ccg acc gta                     1332
Gln Asn Thr Ala Glu Glu Thr Ser Lys Pro Thr Val
        435                 440

<210> SEQ ID NO 2
<211> LENGTH: 444
<212> TYPE: PRT
<213> ORGANISM: Legionella pneumophila

<400> SEQUENCE: 2

Thr Phe Val Leu Lys Glu Phe Asp Ala Leu Lys Ser His Phe Asn Asp
 1               5                  10                  15

Thr Val Lys Ile Ile Leu Gln Arg Glu Lys Lys Asp Lys Ile Glu Asp
             20                  25                  30

Leu Pro Asn Pro Arg Lys Glu Glu Leu Gln Phe Leu Thr Ala Val Leu
         35                  40                  45

Asn Gln Leu Glu Ala Lys Ile Asp Glu Leu Lys Pro Arg Ser Leu Ala
     50                  55                  60

Ser Tyr Val His Val Phe Tyr Gly Ala Met Leu Leu Val Cys Lys Asp
 65                  70                  75                  80

Val Glu Asn Asn Leu Arg Val Met Glu Lys Lys Glu Asn Ser Leu Leu
                 85                  90                  95

Phe Thr Arg Leu Met Asp Gly Met Gly Ile Ser Asp Glu Asn Ile Pro
            100                 105                 110

Thr Ser Glu Gln Asn Ile Met Phe Tyr Arg Gly Leu Asn Lys Phe Leu
        115                 120                 125

Asn Phe Ile Tyr Glu Ser Asn Asp Ser Arg Lys Gly Leu Lys Lys Glu
    130                 135                 140

His Phe Leu Gln Val Leu Ser Leu Lys Lys Ile Tyr Ser Leu Ala Lys
145                 150                 155                 160

Leu Ser Tyr Glu Gln Glu Glu Ala Ala Glu Asn Asn Ala Leu Ala Lys
                165                 170                 175

Leu Thr Ala Asp Gly Lys Thr Lys Ala Asn Ala Asn Ser Phe His Val
            180                 185                 190
```

```
Glu Lys Pro Ile Asp Ser Ser Ile Val Glu Gln Phe Lys Ser Trp Asp
        195                 200                 205
Glu Met Lys Gly Ala Leu His Gln Leu Ile Leu Asp Glu Leu Ser Asp
        210                 215                 220
Lys Asn Val Ala Lys Ile Ser Ala Leu Ser Gln Ala Arg Ser Ala Gln
225                 230                 235                 240
Leu Lys Phe Leu Gln Thr Met Ala Glu Gln Leu Asp Lys Ile Pro Asn
                245                 250                 255
Gln Ser Leu Glu Pro Ser Glu Lys Met Ala Ile Leu Ala Gly Ala Met
                260                 265                 270
Tyr Ile Val Arg Gly Gln Ile Ala Gln Glu Tyr Gly Lys Asp Pro Leu
            275                 280                 285
Ser Asn Asp Lys Ile Ser Ala Thr Val Ile His Thr Gly Leu Ser Thr
        290                 295                 300
Ile Leu His Ala Asn Ala Asp Cys Cys Glu Asp Lys Glu Val Leu Ile
305                 310                 315                 320
Ala Ala Ala Asn Lys Phe Ile Arg His Met Val Ile Glu Arg Pro Glu
                325                 330                 335
Gln Ser Asn Lys Lys Ile Thr Lys Glu Ser Val Arg Gly Asn Asn Met
                340                 345                 350
Phe Ser Asp Ile Ala Gly Phe Gln Leu Ile Ser Val Leu Thr Leu Ile
            355                 360                 365
Gln Asn Met Ile Lys Thr Cys Arg Thr Asp Ala Ile Glu Ala Cys Val
        370                 375                 380
Thr Lys Arg Lys Glu Glu Leu Glu Ala Leu Lys Pro Lys Lys Glu Gly
385                 390                 395                 400
Tyr Ser Ile Ala Ser Ser Val Thr Gly Tyr Val Gly Ser Trp Phe Lys
                405                 410                 415
Lys Ala Pro Ser Met Ser Glu Asp Glu Asp Leu Lys Asp
            420                 425                 430
Gln Asn Thr Ala Glu Glu Thr Ser Lys Pro Thr Val
        435                 440

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgtttgttt taaaggaatt tg                                              22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tacggtcggt ttgctggtc                                                  19
```